United States Patent
Foster et al.

(10) Patent No.: US 10,039,918 B2
(45) Date of Patent: *Aug. 7, 2018

(54) IMPLANTABLE LEAD HAVING A LUMEN WITH A WEAR-RESISTANT LINER

(71) Applicant: Cardiac Pacemakers, Inc., St. Paul, MN (US)

(72) Inventors: Arthur J. Foster, Blaine, MN (US); Daniel J. Foster, Lino Lakes, MN (US); Christopher R. Perrey, Victoria, MN (US); Andrew L. De Kock, Andover, MN (US); Patrick Willoughby, Shoreview, MN (US); Bryan A. Clark, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 122 days.

This patent is subject to a terminal disclaimer.

(21) Appl. No.: 15/137,618

(22) Filed: Apr. 25, 2016

(65) Prior Publication Data

US 2016/0235966 A1    Aug. 18, 2016

Related U.S. Application Data

(63) Continuation of application No. 14/075,515, filed on Nov. 8, 2013, now Pat. No. 9,364,662.

(Continued)

(51) Int. Cl.
*A61B 1/05* (2006.01)
*A61N 1/375* (2006.01)
(Continued)

(52) U.S. Cl.
CPC ............ *A61N 1/056* (2013.01); *A61N 1/0587* (2013.01); *A61N 1/362* (2013.01); *A61N 1/3605* (2013.01);
(Continued)

(58) Field of Classification Search
CPC ........ A61N 1/05; A61N 1/056; A61N 1/0587; A61N 1/36; A61N 1/3605; A61N 1/362; A61N 1/372; A61N 1/375; A61N 1/3752
(Continued)

(56) References Cited

U.S. PATENT DOCUMENTS

| 4,704,240 A | 11/1987 | Reavely et al. |
| 4,707,206 A | 11/1987 | Trepus, Jr. et al. |

(Continued)

FOREIGN PATENT DOCUMENTS

| CN | 102281915 A | 12/2011 |
| CN | 104797290 A | 7/2015 |

(Continued)

OTHER PUBLICATIONS

International Preliminary Examination Report issued in PCT/US2013/069240, completed May 12, 2015, 6 pages.

(Continued)

*Primary Examiner* — Christopher A Flory
(74) *Attorney, Agent, or Firm* — Faegre Baker Daniels LLP

(57) ABSTRACT

An implantable lead includes a lead body having a proximal end portion and a distal end portion. The lead body includes an insulative member having a lumen extending longitudinally between the proximal end portion and the distal end portion. The lead body also includes a generally tubular helical liner disposed coaxially with the lumen within the insulative member. A pitch of the helical liner varies along the length of the lead. The implantable lead also includes an electrode disposed along the lead body in the distal end portion thereof, and a conductor disposed within the lumen and electrically coupled to the electrode. A terminal connector is coupled to the proximal end portion of the lead body and to the conductor.

19 Claims, 6 Drawing Sheets

Related U.S. Application Data

(60) Provisional application No. 61/724,686, filed on Nov. 9, 2012.

(51) Int. Cl.
  *A61N 1/36* (2006.01)
  *A61N 1/05* (2006.01)
  *A61N 1/362* (2006.01)

(52) U.S. Cl.
  CPC ....... *A61N 1/3752* (2013.01); *Y10T 29/49174* (2015.01)

(58) Field of Classification Search
  USPC .......................................... 607/2, 9, 116, 122
  See application file for complete search history.

(56) References Cited

U.S. PATENT DOCUMENTS

| | | |
|---|---|---|
| 4,806,401 A | 2/1989 | Trepus, Jr. et al. |
| 5,062,456 A | 11/1991 | Cooke et al. |
| 5,160,325 A | 11/1992 | Nichols et al. |
| 5,445,859 A | 8/1995 | Lindegren et al. |
| 5,476,501 A | 12/1995 | Stewart et al. |
| 5,529,820 A | 6/1996 | Nomi et al. |
| 5,645,559 A | 7/1997 | Hachtman et al. |
| 5,843,149 A | 12/1998 | Ebert et al. |
| 5,876,430 A | 3/1999 | Shoberg et al. |
| 6,053,171 A | 4/2000 | Stewart et al. |
| 6,078,839 A | 6/2000 | Carson |
| 6,379,596 B1 | 4/2002 | Warburton-Pitt |
| 6,599,275 B1 | 7/2003 | Fischer, Jr. |
| 6,672,338 B1 | 1/2004 | Esashi et al. |
| 6,695,831 B1 | 2/2004 | Tsukada et al. |
| 6,706,364 B2 | 3/2004 | Janusson et al. |
| 6,973,352 B1 | 12/2005 | Tsutsui et al. |
| 7,223,329 B2 | 5/2007 | Esashi et al. |
| 7,985,452 B2 | 7/2011 | Francis et al. |
| 8,306,630 B2 | 11/2012 | Stubbs et al. |
| 8,630,718 B2 | 1/2014 | Stahmann et al. |
| 2003/0120197 A1 | 6/2003 | Kaneko et al. |
| 2003/0181966 A1 | 9/2003 | Morgan |
| 2004/0116848 A1 | 6/2004 | Gardeski et al. |
| 2005/0006009 A1 | 1/2005 | Esashi et al. |
| 2005/0113862 A1 | 5/2005 | Besselink et al. |
| 2009/0071686 A1 | 3/2009 | Boser et al. |
| 2009/0076580 A1 | 3/2009 | Boser et al. |
| 2010/0179630 A1 | 7/2010 | Williams |
| 2010/0228331 A1 | 9/2010 | Conger |
| 2010/0234929 A1 | 9/2010 | Scheuermann |
| 2011/0112476 A1 | 5/2011 | Kauphusman et al. |
| 2011/0160816 A1 | 6/2011 | Stubbs et al. |
| 2011/0160829 A1 | 6/2011 | Foster et al. |
| 2011/0218603 A1 | 9/2011 | Victorine et al. |
| 2011/0251519 A1 | 10/2011 | Romoscanu |
| 2012/0172717 A1 | 7/2012 | Gonda |
| 2013/0158479 A1 | 6/2013 | Kauphusman et al. |
| 2014/0074201 A1 | 3/2014 | Arnholt et al. |
| 2014/0135885 A1 | 5/2014 | Foster et al. |
| 2014/0257445 A1 | 9/2014 | Weber et al. |

FOREIGN PATENT DOCUMENTS

| | | |
|---|---|---|
| JP | H08215312 A | 8/1996 |
| JP | 2003047653 A | 2/2003 |
| JP | 2012045043 A | 3/2012 |
| WO | 2011028873 A2 | 3/2011 |

OTHER PUBLICATIONS

International Search Report and Written Opinion issued in PCT/US2013/069240, dated Jan. 8, 2014.

IMPLANTABLE LEAD HAVING A LUMEN WITH A WEAR-RESISTANT LINER

CROSS-REFERENCE TO RELATED APPLICATION

This application is a continuation of U.S. application Ser. No. 14/075,515, filed Nov. 8, 2013, which claims priority to U.S. Provisional Application 61/724,686, filed Nov. 9, 2012, all of which are herein incorporated by reference in their entirety.

TECHNICAL FIELD

The present invention relates to an implantable system having an implantable lead. More specifically, the invention relates to a wear-resistant implantable lead for an implantable system.

BACKGROUND

Generally, an implantable system includes an implantable medical device (IMD) having a power source and stimulation electronics, and a lead system connected to the IMD. The lead system includes one or more flexible implantable leads, each having a lead body housing a conductor therein and an electrode disposed along the lead body and electrically coupled to the conductor.

There exists a continuing need for improved implantable lead configurations.

SUMMARY

In Example 1, the present disclosure describes an implantable lead comprising a lead body, an electrode, a conductor, and a terminal connector. The lead body has a proximal end portion and a distal end portion, and includes an insulative member having a lumen extending longitudinally through the proximal end portion and the distal end portion, and a generally tubular liner helical liner disposed coaxially with the lumen within the insulative member. A pitch of the helical liner varies along the length of the lead. The electrode is disposed along the lead body in the distal end portion thereof. The conductor is disposed within the lumen and is electrically coupled to the electrode. The terminal connector is coupled to the proximal end portion of the lead body and to the conductor, and is configured to provide an electrical and mechanical connection of the implantable lead with an implantable medical device.

In Example 2, the implantable lead of Example 1, wherein the helical liner is in the form of a strand of material helically wound into generally tubular shape.

In Example 3, the implantable lead of either of Examples 1 or 2, wherein the helical liner is a tubular member having a wall including the inner surface and an outer surface, and at least one slot extending through the wall.

In Example 4, the implantable lead of Example 3, wherein the slot extends longitudinally along a portion of the tubular member and in a helical path about a circumference of the lumen.

In Example 5, the implantable lead of either of Examples 3 or 4, wherein the tubular member includes an electrode segment devoid of any portion of the slot, and wherein the electrode segment is positioned adjacent to the electrode.

In Example 6, the implantable lead of any of Examples 3-5, wherein the tubular member includes at least one connecting strut spanning the slot in at least one location along a length of the slot.

In Example 7, the implantable lead of any of Examples 1-6, wherein the helical liner is partially or wholly embedded within the insulative member.

In Example 8, the implantable lead of any of Examples 1-7, wherein the lumen is a first lumen, the helical liner is a first helical liner, the lead body further including a second lumen, a second generally tubular helical liner, a second conductor and a second electrode. The second lumen extends between the proximal end portion and the distal end portion of the lead body. The second generally tubular helical liner is disposed coaxially with the second lumen within the insulative member. The second conductor extends within the second lumen and is electrically connected to the second electrode, which is disposed along the distal end portion of the lead body.

In Example 9, the implantable lead of Example 8, wherein a pitch of the second helical liner varies along the length of the lead.

In Example 10, the present disclosure describes a method of manufacturing an implantable lead. The method comprising forming an insulative lead body having a proximal end portion and a distal end portion, the lead body including an insulative member with a lumen extending longitudinally through the proximal end portion and the distal end portion, and a generally tubular helical liner disposed coaxially with the lumen within the insulative member, a pitch of the helical liner varying along the length of the lead. The method further comprises coupling an electrode to the lead body in the distal end portion thereof, and coupling a terminal connector to the proximal end portion of the lead body. The method also comprises coupling a conductor positioned within the lumen to the electrode and to the terminal connector.

In Example 11, the method of Example 10, wherein forming the insulative lead body includes disposing a first material defining the helical liner over a mandrel, and forming the insulative member by disposing a second material over the first material, the second material being different than the first material.

In Example 12, the method of Example 11, wherein disposing the first material over the mandrel includes helically winding a ribbon of the first material around the mandrel In Example 13, the method of either of Examples 11 or 12, wherein the mandrel is a core pin, a cable conductor, a coil conductor, or a tubular sleeve.

In Example 14, the method of any of Examples 11-13, further comprising removing the mandrel after forming the insulative member, and positioning the conductor within the lumen after removing the mandrel.

In Example 15, the method of any of Examples 11-14, wherein forming the insulative member includes molding or extruding the second material over the first material, wherein the second material is an electrically insulative material.

In Example 16, the method of Example 10, wherein forming the insulative lead body includes forming the insulative member and disposing the generally tubular liner within the lumen.

In Example 17, the present disclosure describes another method of manufacturing an implantable lead. The method comprises forming an insulative lead body having a proximal end portion and a distal end portion, the lead body including an insulative member with a lumen extending longitudinally through the proximal end portion and the distal end portion, and a generally tubular helical liner disposed coaxially with the lumen within the insulative member, a pitch of the helical liner varying along the length of the lead. The method further comprises coupling an electrode to the lead body in the distal end portion thereof, and positioning a conductor within the lumen, the conductor having a proximal end and an opposite distal end. The method also comprises coupling the distal end of the conductor with the electrode, and coupling a terminal connector to the proximal end portion of the lead body and to the proximal end of the conductor.

In Example 18, the method of Example 17, wherein forming the insulative lead body includes helically winding a ribbon of a first material around a mandrel to form the helical liner, and forming the insulative member by disposing a second material over the first material, the second material being different than the first material.

In Example 19, the method of Example 17, wherein forming the insulative lead body includes forming the insulative member, helically winding a ribbon of a first material to form the helical liner, and disposing the helical liner within the lumen.

In Example 20, the method of either of Examples 18 or 19, wherein the first material is a flexible, electrically insulating polymer.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 6 is a partial elevation view of a tubular liner for an implantable lead body according to another embodiment of the present invention.

Figure 1:
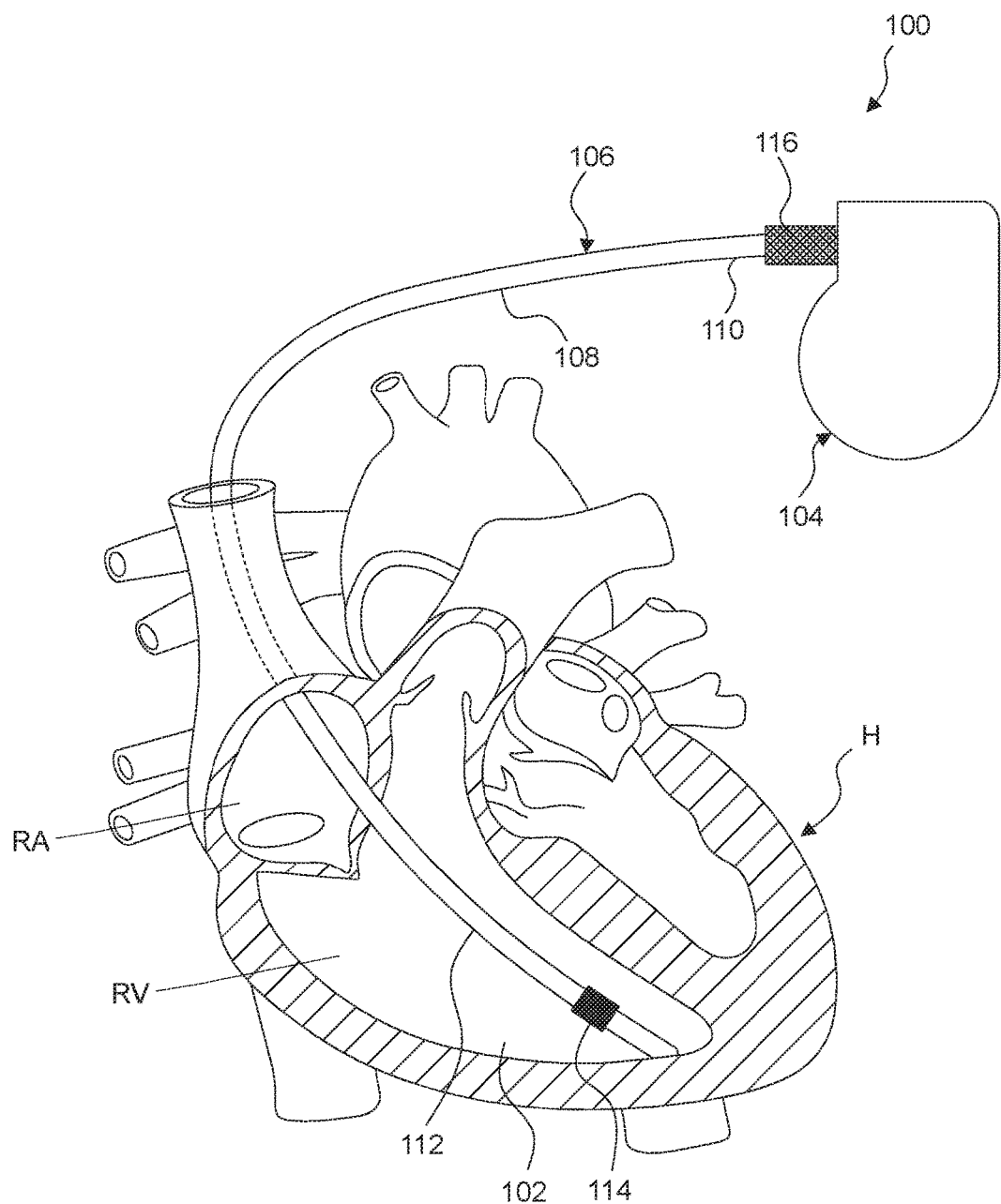
FIG. 1 is a schematic illustration of an implantable system having an implantable lead and an IMD in an implanted state, according to an embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration of an implantable system 100 including an implantable medical device ("IMD") 104 and an implantable lead 106 connected to the IMD 104 and partially implanted within a chamber of a patient's heart H. The implantable lead 106 includes a lead body 108 having a proximal end portion 110 and a distal end portion 112. The lead body 108 further includes an electrode 114 disposed along the lead body 108 in the distal end portion 112 thereof, and a terminal connector 116 coupled to the proximal end portion 110 of the lead body 108. The terminal connector 116 is configured to provide an electrical and mechanical connection of the implantable lead 106 with the IMD 104. For example, the IMD 104 includes a port (not shown) adapted to receive a portion of the terminal connector 116 to establish the electrical and mechanical connection therebetween.

In various embodiments, the IMD 104 can be implanted subcutaneously within an implantation location or pocket in the patient's chest or abdomen. The IMD 104 may be an implantable medical device known in the art or later developed, for delivering an electrical therapeutic stimulus to the patient. In various embodiments, the IMD 104 can be a pacemaker, an implantable cardioverter defibrillator (ICD) device, or a cardiac resynchronization therapy (CRT) device. In various embodiments, the IMD 104 may include both defibrillation and pacing/CRT capabilities (e.g., a CRT-D device).

The lead 106 operates to convey electrical signals and stimuli between the heart H and the IMD 104. The electrical signals and stimuli conveyed by the lead 106 are carried to/from the electrode 114 by one or more conductors disposed within the lead body 108. The terminal connector 116 is both mechanically and electrically coupled to the aforementioned conductor(s), and operates to both mechanically and electrically couple the lead 106 to the IMD 104. The terminal connector 116 and the electrode 114 can take on configurations known in the art, whether now known or later developed. In addition, while in the illustrated embodiment the lead 106 includes one electrode 114, in other embodiments, the lead 106 can include additional electrodes (e.g., a tip electrode and/or additional electrodes along the length of the lead body 108).

In the illustrated embodiment, the lead 106 is implanted in the right ventricle RV. In other embodiments, the CRM system 100 may include additional leads, e.g., a lead implanted in the right atrium RA, and/or a lead extending into a coronary vein for stimulating the left ventricle in a bi-ventricular pacing or cardiac resynchronization therapy system.

In the various embodiments, the lead body 108 is a flexible, tubular structure formed primarily from an electrically insulative material. As will be explained in greater detail herein, in various embodiments, the lead body 108 is configured so as to minimize wear and abrasion of internal surfaces of the lead body 108 that are in contact with other lead components, in particular, the aforementioned conductors disposed within the lead body 108 for electrically coupling the lead electrode 114 to circuitry and hardware in the IMD 104.

Figure 2:
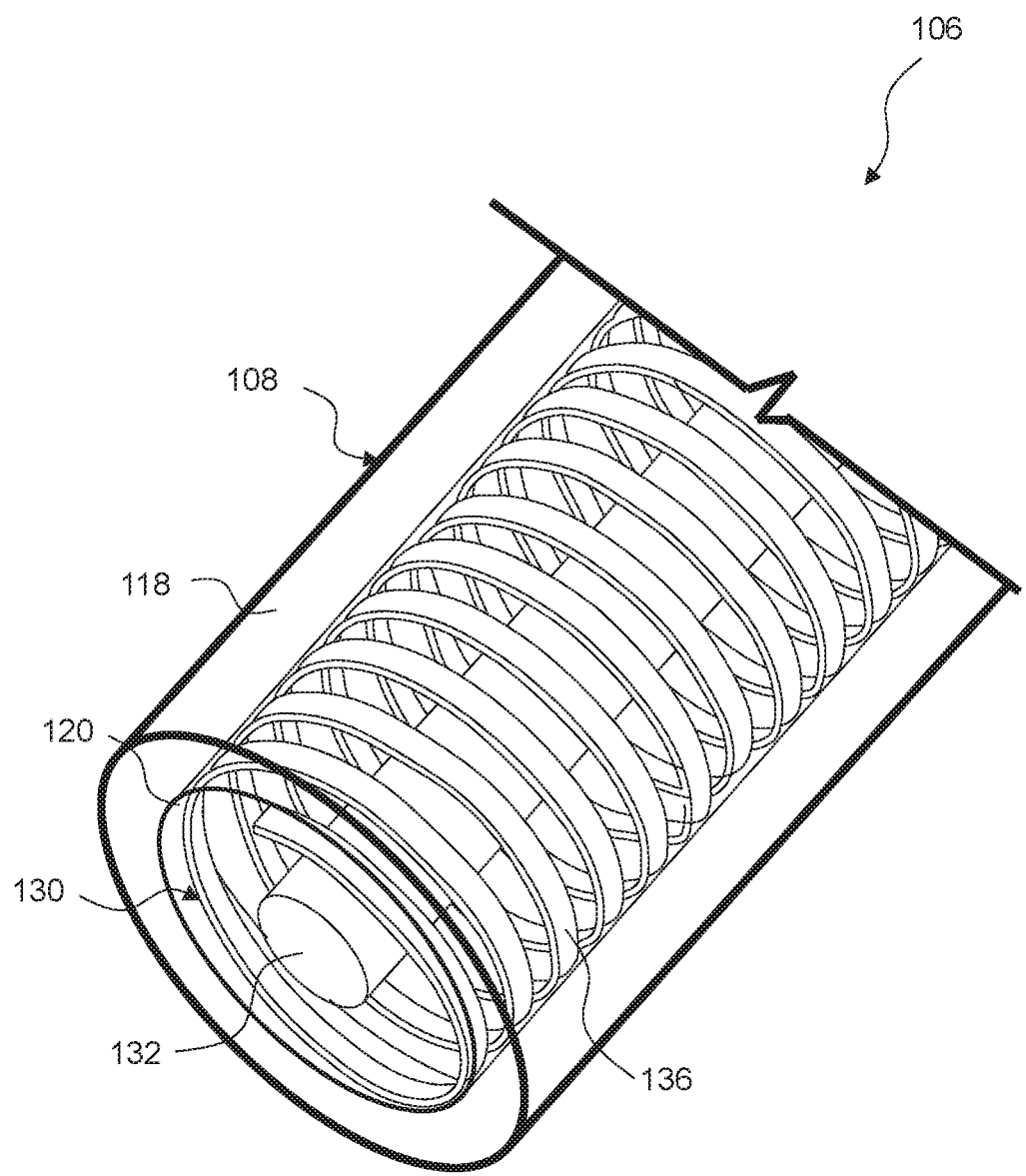
FIG. 2 is an enlarged perspective view of a portion of the implantable lead of FIG. 1, according to an embodiment.

FIG. 2 is an enlarged perspective view of a portion of the implantable lead 106 according to one embodiment. As shown, the lead body 108 includes a tubular insulative member 118 having a lumen 120, and a generally tubular liner 130. In the various embodiments, the lumen 120 extends longitudinally within the insulative member 118 from the proximal end portion 110 and at least partially through the distal end portion 112 of the lead body 108 (shown in FIG. 1). In addition, the liner 130 is disposed coaxially with the lumen 120 within the insulative member 118. As further shown, the implantable lead 106 also includes a conductor 132 disposed within the lumen 120. The conductor 132 is electrically coupled to the electrode 114 and to an electrical contact on the terminal connector 116 (see FIG. 1). The conductor 132 can be a single or multi-filar conductor coil, or alternatively, a single- or multi-strand conductor cable. In addition, the conductor 132 can, in various embodiments, be bare, or can be covered by an electrical insulating material. In short, the various embodiments are not limited to any particular configuration of the conductor 132.

The insulative member 118 provides structure for the lead 106 as a whole, and also operates to electrically insulate the conductor 132 from the external environment. The insulative member 118 can be made of a biocompatible electrically insulative material now known or later developed for use in implantable leads. Exemplary insulative materials for forming the insulative member 118 can include, without limitation, silicone rubbers, polyurethanes, and co-polymers thereof.

In the illustrated embodiment, the liner 130 is in the form of a ribbon of material 136 which is helically wound to form a generally tubular member and disposed within the insulative member 118 so as to surround the lumen 120. In various embodiments, the liner 130 extends along at least the length of the lumen 120 through which the conductor 132 also extends.

In one embodiment, the liner 130 is disposed within the lumen 120 such that the liner 130 bears radially against an inner surface of the insulative member 118 defining the lumen 120. In one embodiment, the liner 130 can be embedded partially within the insulative member 118. In the foregoing embodiments, the liner 130 can define an inner surface against which the conductor 132 can bear. In some embodiments, the liner 130 can be completely embedded within the insulative member 118, such that a thin layer of the material forming the insulative member 118 lies radially inward of the liner 120.

During use, the lead 106 can be subjected to motion due to the regular, cyclic motion of the heart H (see FIG. 1). In addition to the consequent relative motion between the heart H and the lead 106, the internal components of the lead 106, in particular, the conductor 132 and the insulative member 118 of the lead body 108, can move relative to one another. The liner 130 can operate to enhance the structural integrity of the insulative member 118, and in particular, to substantially inhibit wear and abrasion of the insulative member 118 that, but for the presence of the liner 130, could otherwise occur due to contact and relative motion of the inner surface of the lumen 120 and the conductor 132.

In various embodiments, the liner 130 can also be configured to provide a pre-determined flexibility profile to the lead 106 as a whole. For example, in various embodiments, the pitch of the helically-wound ribbon 136 can be selected so as to control the flexibility of the lead 106, with a closer pitch generally resulting in an increase in the stiffness of the lead 106. In various embodiments, the pitch of the helically-wound ribbon can be varied along the length of the lead 106, such that respective regions of the lead 106 exhibit different flexibilities.

In various embodiments, the ribbon of material 136 can be made from a flexible, relatively lubricious, electrically insulative material such as, without limitation, polyurethanes, parylene, polytetrafluoroethylene (PTFE), ethylene tetrafluoroethylene (ETFE), perfluoroalkoxy (PFA), polyether ether ketone (PEEK), high density polyethylene (HDPE), and polypropylene (PP).

In one exemplary embodiment, the lead body 108 can be manufactured by separately forming the insulative member 118 and the liner 130, and thereafter mounting the liner 130 within the lumen 120. For example, in one embodiment, the insulative member 118 can be formed according to known techniques (e.g., molding, extrusion), and the ribbon 136 can be helically wound about a mandrel sized such that the outer dimension of the wound ribbon 136 is less than the inner diameter of the lumen 120. In one embodiment, the ribbon 136 can be configured to exhibit sufficient resiliency and can be twisted and stretched as it is wound about the mandrel and fixed in this twisted/stretched configuration. Thereafter, the mandrel with the ribbon 136 wound thereabout can be inserted into the lumen 120, and the mandrel can subsequently be removed, allowing the wound ribbon 136 to radially expand against the inner surface of the lumen 120 to form the liner 130. In another exemplary embodiment, the ribbon 136 can be helically wound about a mandrel having the desired inner diameter of the lumen 120, and the insulative member 118 can thereafter be formed over the wound ribbon 136 and mandrel. Exemplary forming processes suitable for forming the insulative member 118 over the ribbon 136 can include, without limitation, extrusion, overmolding, dip coating, spray coating and chemical vapor deposition processes. In such embodiments, the ribbon 136 will be partially or wholly embedded within the insulative member 118 to form the liner 130.

In one embodiment, the mandrel may be a core pin, tubular sleeve, or comparable structure specifically designed for manufacturing the lead body 108 with the liner 130. In another embodiment, the mandrel can be the conductor 132 itself.

In various other embodiments, the liner 130 can be formed from a generally cylindrical hypotube of the aforementioned materials, and can be machined to form the helical liner 130 shown in FIG. 2. Exemplary manufacturing techniques for forming the liner 130 in this way can include, without limitation, micro-machining processes, laser ablation, water jet cutting, and the like. In such embodiments, the liner 130 can be inserted into the lumen 120 after separately forming the insulative member 118, or alternatively, can be disposed over a mandrel and the insulative member 118 can be formed over the liner as described previously.

Figure 3:
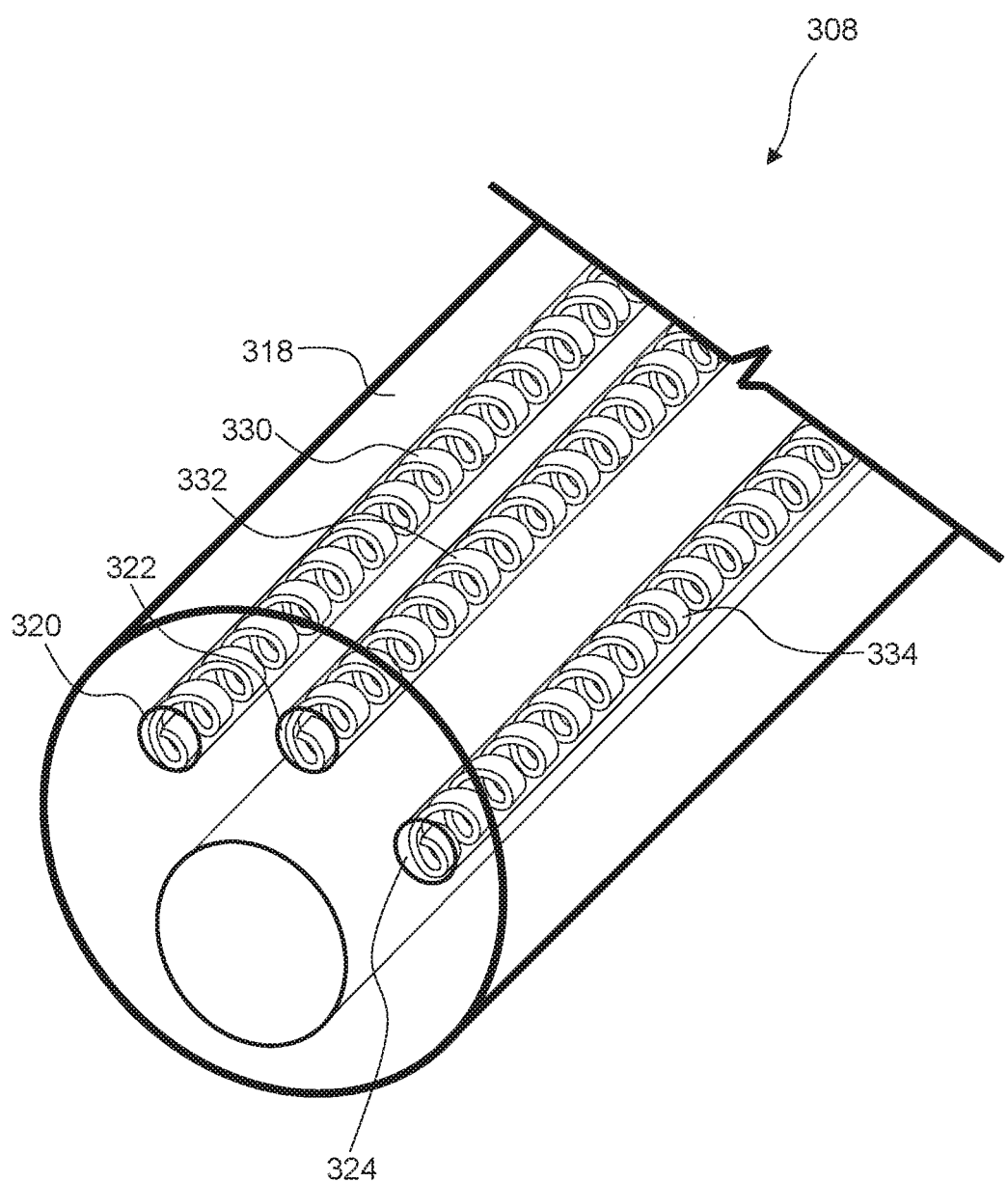
FIG. 3 is a perspective view of a portion of a lead body for use in a multi-polar lead, according to an embodiment.

FIG. 3 is a schematic illustration of a portion of an alternative lead body 308 for a multi-polar implantable lead according to various embodiments. As shown in FIG. 3, the lead body 308 includes a multi-lumen insulative member 318 including a first lumen 320, a second lumen 322, and a third lumen 324. As further shown, the lead body 308 further includes a first liner 330, a second liner 332, and a third liner 334 disposed coaxially with the first, second, and third lumens 320, 322, 324, respectively, within the insulative member 318. As will be appreciated, each of the lumens 320, 322, 324 can receive a respective conductor element, with each conductor element being coupled to an electrode and an electrical contact on a terminal connector similar to the terminal connector 116 of the lead 106 (see FIG. 1) but configured for use on the multi-polar lead.

As shown, the first, second, and third liners 330, 332, 334 are each in the form of a ribbon of material 340, 342, 344, respectively, each of which is helically wound to form a generally tubular member and disposed within the insulative member 318 so as to surround, respectively, the lumens 320, 322, 324. In the various embodiments, the liners 330, 332, 334 can be configured and manufactured in substantially the same or in an identical manner as the liner 130 of the lead 106 described herein.

Like the liner 130, the liners 330, 332, 334 can enhance the structural integrity of the insulative member 318, and in particular, can substantially inhibit wear and abrasion of the insulative member 318 that, but for the presence of the liners 330, 332, 334, could otherwise occur due to contact and relative motion of the inner surface of the lumen 120 and the conductor (not shown) disposed in the lumens 320, 322, 324.

Figure 4A:
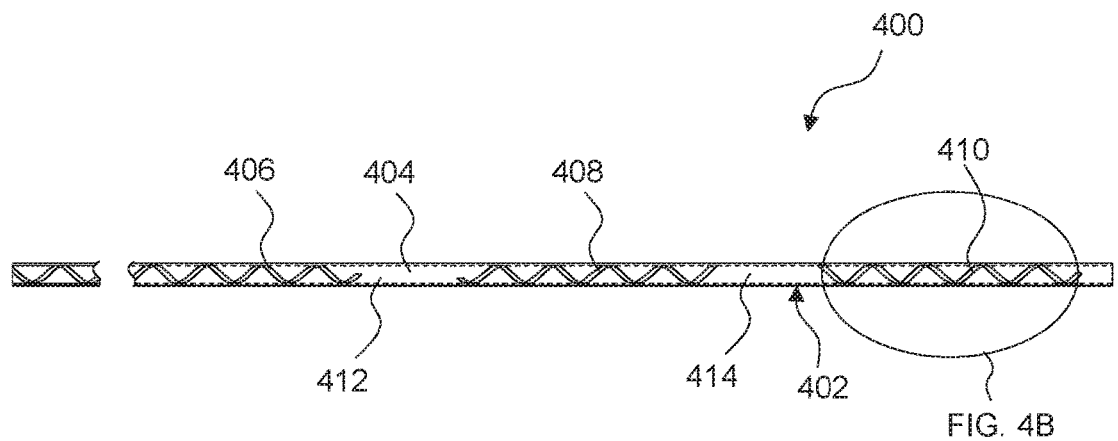
FIGS. 4A and 4B are elevation views of a tubular liner for use in an implantable lead according to an alternative embodiment.
Figure 4B:
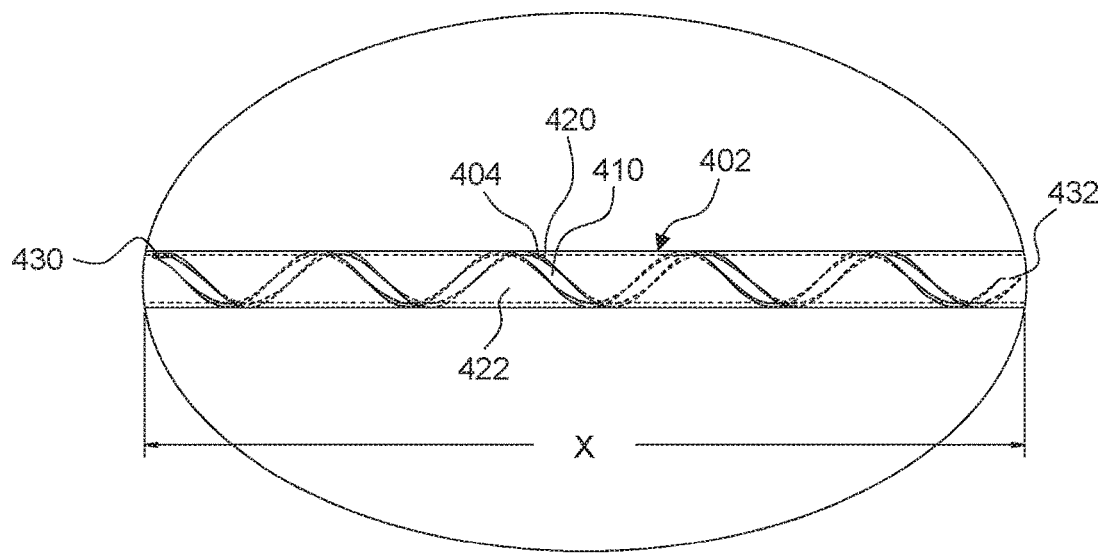

FIGS. 4A and 4B are partial elevation views of a tubular liner 400 for an implantable lead body (e.g., the lead body 108 or 308) according to another embodiment. In the illustrated embodiment, the liner 400 includes a tubular member 402 having a wall 404 and a plurality of slots 406, 408, 410 extending through the wall 404 and disposed along the tubular member 402, and a pair of electrode segments 412, 414. As shown, each of the slots 406, 408, 410 extends longitudinally in a helical path along a portion of the tubular member 402 for a defined length. As further shown, each of the electrode segments 412, 414 is devoid of any portion of a slot, with the electrode segment 412 being located between the slots 406, 408, and the electrode segment 414 being located between the slots 408, 410. The electrode segments 412, 414, when present, are located so as to be positioned adjacent to an electrode, such as the electrode 114 of the lead 106 (see FIG. 1), in the assembled lead. For example, in multi-polar leads, a plurality of electrodes may be axially spaced along the length of the lead body, and various conductors may extend through regions of the lead containing electrodes to which the respective electrodes are not intended to be electrically coupled. The electrode segments 412, 414, when present, operate to protect against unintended electrical short circuits between such conductors and electrodes.

As can be seen in the enlarged view of FIG. 4B, the wall 404 of the tubular member 402 includes an inner surface 420 and an outer surface 422. Further, the portion of the tubular member 402 is shown to include a length X, and the slot 410 extends longitudinally along the length X and in a helical path about the circumference of the tubular member 402. As further shown, the slot 410 extends radially through the wall 404 from the inner surface 420 to the outer surface 422. As further shown in the illustrated embodiment, the slot 410 has a first end 430 and a second end 432, and is continuous and uninterrupted between the first and second ends 430, 432.

The liner 400 is configured to be disposed coaxially with a lead body lumen in the same manner as the liners 130, 330 described herein, and are thus configured to operate and provide substantially the same or identical advantages as the liners 130, 330. In the various embodiments, the slots 406, 408, 410 provide the liner 400 and, consequently, the lead in which the liner 400 is disposed, with a desired degree of flexibility. As discussed herein, the electrode segments 412, 414 are located so as to be positioned adjacent to an electrode, such as the electrode 114 of the lead 106 (see FIG. 1), in the assembled lead, to provide an uninterrupted insulative liner in the region(s) of the lead containing the electrode(s) and thereby protect against short circuits in the event of a failure of the electrical insulation on the lead conductor(s) in these regions.

Figure 5:
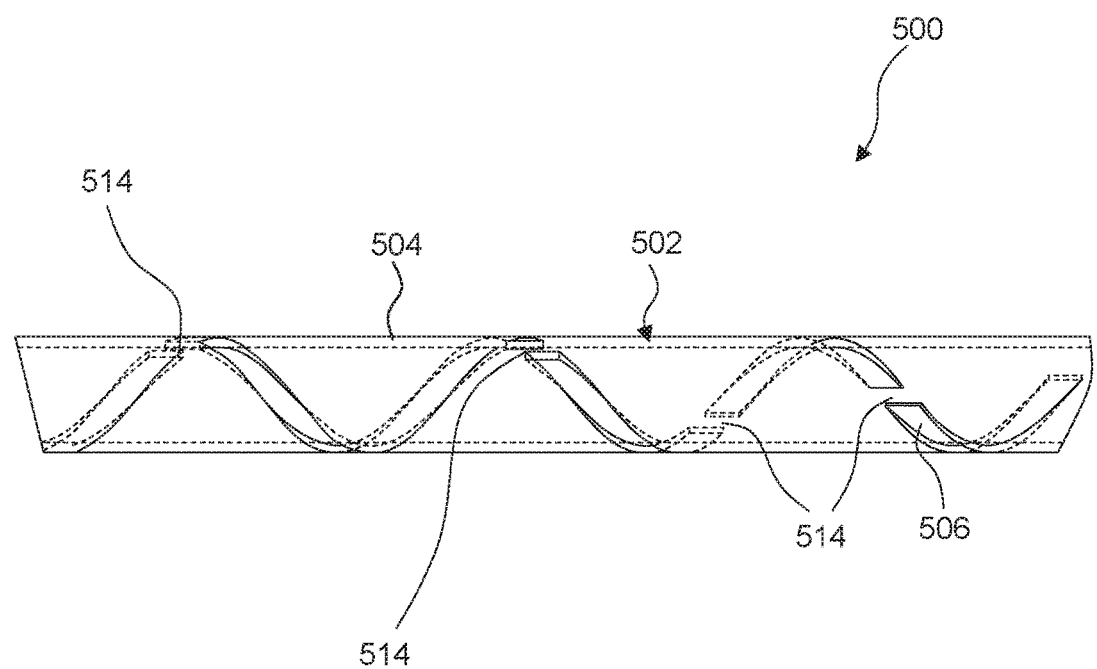
FIG. 5 is a partial elevation view of a tubular liner for an implantable lead body according to another embodiment.

FIG. 5, illustrates an elevation view of a portion of a tubular liner 500 according to another embodiment. In the illustrated embodiment, the liner 500 is substantially structurally and functionally similar to the liner 400 as described in conjunction with the FIG. 4, and includes a tubular member 502 having a wall 504 and a slot 506 extending through the wall and in a helical path around the circumference of the tubular member 502 along a portion of the length thereof. In addition, the liner 500 includes a plurality of connecting struts 514 spanning the width of the slot 506 at pre-determined intervals along the length of the slot 506. The connecting struts 514 operate to enhance the axial and flexural strength of the liner 500 and, consequently, the lead in which the liner 500 is disposed. In various embodiments, the number, location and/or spacing of the connecting struts 514 can be selected to provide a desired degree of axial and/or flexural stiffness in the liner 500.

FIG. 6 is a partial elevation view of a tubular liner 600 for an implantable lead body (e.g., the lead body 108 or 308) according to another embodiment. The liner 600 includes a plurality of longitudinally-spaced cylindrical segments, such as a first cylindrical segment 602, a second cylindrical segment 604, a third cylindrical segment 606 and a fourth cylindrical segment 608. The liner 600 also includes a plurality of connecting struts such as first connecting struts 612, second connecting struts 614, and third connecting struts 616. As shown, the first, second and third connecting struts 612, 614, 616 extend between and connect the adjacent first, second, third and fourth cylindrical segments 602, 604, 606, 608. In addition, the liner 600 also includes a plurality of cylindrical electrode segments 620 positioned at selected locations along the length of the liner 600, which locations are selected to correspond to the locations of electrodes on the fully assembled lead, as described elsewhere herein. In the illustrated embodiment, the electrode segments 620 have longer axial lengths than the cylindrical segments 602, 604, 606, 608, and operate to substantially fully insulate the region(s) of the lead containing the electrode(s) and thereby protect against short circuits in the event of a failure of the electrical insulation on the lead conductor(s) in these regions. In the various embodiments, the liner 600 may have one electrode segment 620 to correspond to each electrode located along the length of the corresponding lead body, although this is not a requirement of the various embodiments.

Figure 6C:
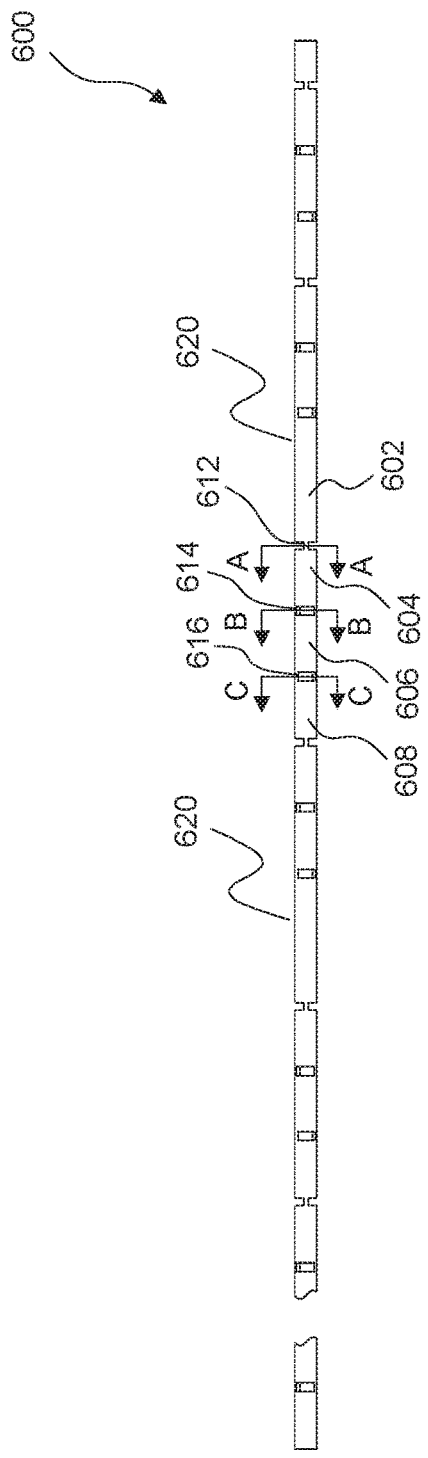
FIGS. 6A-6C are cross-sectional views of the tubular liner of the FIG. 6.
Figure 6C:
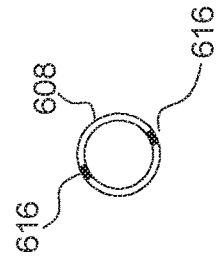
Figure 6B:
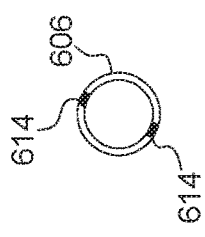
Figure 6A:
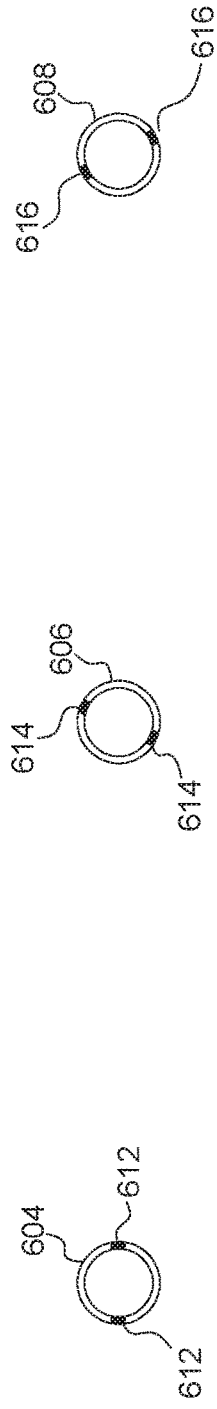

FIGS. 6A-6C are cross-sectional views of the liner 600 taken along lines A-A, B-B, and C-C, respectively, showing the orientations of the various connecting struts 612, 614, 616. As shown, in the illustrated embodiment, each of the first, second, and third connecting struts 612, 614, 616 are arranged as pairs of connecting struts. As further shown, in the illustrated embodiment, the struts in each pair are disposed about 180 degrees apart from one another with respect to the circumference of the respective cylindrical segments. For example, FIG. 6A illustrates the first connecting struts 612 being disposed about 180 degrees apart with respect to the circumference of the second cylindrical member 604. Similarly, the second and third connecting struts 614, 616 are disposed about 180 degrees apart with respect to the circumference of the third and fourth cylindrical members 606 and 608, respectively, as shown in FIGS. 6B-6C. In addition, in the illustrated embodiment, the struts in each pair of connecting struts 612, 614, 616 are radially offset from the struts in each adjacent pair of connecting struts. As shown, the first connecting struts 612 are radially offset from the second connecting struts 614 by about 120 degrees in an anti-clockwise direction, and similarly the second connecting struts 614 are radially offset from the third connecting struts 616 at about 120 degrees in the anti-clockwise direction.

In various embodiments, the orientation of the connecting struts in a particular pair of connecting struts, or the relative orientation of struts in one pair of connecting struts relative to an adjacent pair of connecting struts, can be varied from that shown in FIGS. 6 and 6A-6C so as to tailor the flexural properties of the liner 600 and, consequently, the lead in which the liner 600 is disposed. For example, the physical properties (e.g., length, wall thickness, and the like) of each cylindrical segment can be selected to provide a desired stiffness profile in the liner 600. Similarly, the number, width, thickness, etc. of each of the connecting struts between adjacent cylindrical segments can also be selected to affect the stiffness profile of the liner 600. Additionally, in various embodiments, adjacent cylindrical segments may be connected by a single connecting strut or by more than two connecting struts, which will also affect the flexibility of the liner 600.

Thus, the liners of the various embodiments can advantageously facilitate selectively tailoring the axial and/or lateral flexibility of regions of the lead for their particular operating environment. For example, leads of the various embodiments can include pre-formed regions having pre-defined shapes (e.g., J-shapes or spiral shapes) for directing the electrode(s) toward a particular region to be stimulated and/or for facilitating fixation of the lead in the desired implantation location. In various such embodiments, the portions of the liner(s) within these pre-formed regions may be configured to have relatively high flexibility compared to other regions of the lead and/or may be configured to have different flexibilities in different planes (e.g., so as to be relatively flexible in response to loads applied in one or more directions but relatively stiff in response to loads applied in other directions).

The tubular liners 400, 500, 600 can be formed using a range of manufacturing processes. In various embodiments, the liners 400, 500, 600 can be formed from a hypotube of an electrically insulative material having desired lubricity, strength and flexibility. Exemplary materials for such hypotubes can include, without limitation, any of the materials listed herein for use in the liners 130, 330. Exemplary manufacturing techniques suitable for forming the liners 400, 500, 600 from the aforementioned hypotubes can include, without limitation, micro-machining processes, laser ablation, water jet cutting, and the like.

It is emphasized that the particular configurations of the liners 130, 330, 400, 500, 600 described herein are exemplary only, and that other liner configurations can be employed within the scope of the various embodiments. For example in various embodiments, the liners 130, 330, 332, 334 can be formed from strands of material having cross-sectional shapes (e.g., round, elliptical, square, etc.) other than the flat ribbon shape shown in FIG. 2. Other configurations for the various liner embodiments can include, without limitation, stent-like patterns, irregularly-cut patterns, woven mesh, random mesh, and the like.

In addition, various manufacturing techniques can be utilized to manufacture the lead bodies including the conductor lumen liners 130, 330, 400, 500, 600 (and variations thereof), as well as the implantable leads incorporating such lead bodies. In various embodiments, the liner and the insulative member of the lead body (including one or more conductor lumens) may each be separately formed in its entirety, and the liner can be strung within the corresponding lumen in the insulative member. The coil or cable conductor can then be strung within the lumen including the liner, and the electrode and terminal connector (see FIG. 1) can be coupled to the lead body and the ends of the conductor to substantially complete the lead manufacturing process.

In various other embodiments, a mandrel can be used in the manufacture of the lead body and the corresponding lead. In one embodiment, the liner, such as the liner 130, can itself be formed over a mandrel as described herein. In other embodiments, the liner can be pre-formed to assume the desired configuration, and thereafter slid or otherwise disposed over the mandrel. The insulative member can then be formed over the liner by disposing a second insulative material (such as those described herein) over the liner, the second material being different than the material forming the liner. The various embodiments are not limited to any particular process for forming the insulative member over the liner. Exemplary processes for forming the insulative member over the liner may include, without limitation, extrusion, overmolding, dip coating, spray coating and chemical vapor deposition processes. In various embodiments in which the insulative member is formed over the liner, the liner may be partially or fully embedded in the material forming the insulative member.

In one embodiment, the mandrel may be the coil or cable conductor incorporated in the assembled lead. In such embodiments, upon forming the lead body with the liner as described previously, the terminal connector and electrode (see FIG. 1) can be coupled to the lead body and to the conductor. In other embodiments, the mandrel may be a core pin, tubular sleeve, or comparable structure specifically designed for manufacturing the lead body. In such embodiments, the mandrel is removed after forming the insulative member over the liner. The coil or cable conductor can then be disposed within the lumen including the liner, and the terminal connector and electrode can be coupled to the lead body and to the conductor.

Of course, in the case of a multi-polar lead (e.g., a lead having a lead body such as the lead body 300), the manufacturing processes described herein may be modified to accommodate the additional electrodes, conductors, and conductor lumens having the liners according to the various embodiments.

It is emphasized that the implantable leads of the various embodiments are not limited to cardiac leads such as the lead 106. Rather, other implantable lead applications, such as those configured for neurostimulation, e.g., Spinal Cord Stimulation (SCS), Deep Brain Stimulation (DBS), and Functional Electrical Stimulation (FES), are also contemplated within the scope of the various embodiments.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable lead comprising:
a lead body having a proximal end portion and a distal end portion, the lead body including:
an insulative member having a lumen extending longitudinally through the proximal end portion and the distal end portion; and
a generally tubular helical liner disposed coaxially with the lumen within the insulative member, wherein a pitch of the helical liner varies along the length of the lead;
an electrode disposed along the lead body in the distal end portion thereof;
a conductor disposed within the lumen and electrically coupled to the electrode; and
a terminal connector coupled to the proximal end portion of the lead body and to the conductor, the terminal connector configured to provide an electrical and mechanical connection of the implantable lead with an implantable medical device,
wherein the liner defines an inner surface adjacent to the conductor and against which the conductor can bear.

2. The implantable lead of claim 1, wherein the helical liner is in the form of a strand of material helically wound into a generally tubular shape.

3. The implantable lead of claim 1, wherein the helical liner is a tubular member having a wall including an inner surface and an outer surface, and at least one slot extending through the wall.

4. The implantable lead of claim 3, wherein the slot extends longitudinally along a portion of the tubular member and in a helical path about a circumference of the lumen.

5. The implantable lead of claim 4, wherein the tubular member includes an electrode segment devoid of any portion of the slot, and wherein the electrode segment is positioned adjacent to the electrode.

6. The implantable lead of claim 3, wherein the tubular member includes at least one connecting strut spanning the slot in at least one location along a length of the slot.

7. The implantable lead of claim 1, wherein the lumen is a first lumen, the helical liner is a first helical liner, the lead body further including:
- a second lumen extending between the proximal end portion and the distal end portion;
- a second generally tubular helical liner disposed coaxially with the second lumen within the insulative member; and
- a second conductor extending within the second lumen and electrically connected to a second electrode disposed along the distal end portion of the lead body.

8. The implantable lead of claim 7, wherein a pitch of the second helical liner varies along the length of the lead.

9. A method of manufacturing an implantable lead, the method comprising:
- forming an insulative lead body having a proximal end portion and a distal end portion, the lead body including an insulative member with a lumen extending longitudinally through the proximal end portion and the distal end portion, and a generally tubular helical liner disposed coaxially with the lumen within the insulative member, a pitch of the helical liner varying along the length of the lead;
- coupling an electrode to the lead body in the distal end portion thereof;
- coupling a terminal connector to the proximal end portion of the lead body; and
- coupling a conductor positioned within the lumen to the electrode and to the terminal connector, wherein the conductor is adjacent to the liner and can bear against the liner.

10. The method of claim 9, wherein forming the insulative lead body includes:
- disposing a first material defining the helical liner over a mandrel; and
- forming the insulative member by disposing a second material over the first material, the second material being different than the first material.

11. The method of claim 10, wherein disposing the first material over the mandrel includes helically winding a ribbon of the first material around the mandrel.

12. The method of claim 10, wherein the mandrel is a core pin, a cable conductor, a coil conductor, or a tubular sleeve.

13. The method of claim 10, further comprising:
- removing the mandrel after forming the insulative member; and
- positioning the conductor within the lumen after removing the mandrel.

14. The method of claim 10, wherein forming the insulative member includes molding or extruding the second material over the first material, wherein the second material is an electrically insulative material.

15. The method of claim 9, wherein forming the insulative lead body includes forming the insulative member and disposing the generally tubular helical liner within the lumen.

16. A method of manufacturing an implantable lead, the method comprising:
- forming an insulative lead body having a proximal end portion and a distal end portion, the lead body including an insulative member with a lumen extending longitudinally through the proximal end portion and the distal end portion, and a generally tubular helical liner disposed coaxially with the lumen within the insulative member, a pitch of the helical liner varying along the length of the lead;
- coupling an electrode to the lead body in the distal end portion thereof;
- positioning a conductor within the lumen, the conductor having a proximal end and an opposite distal end, wherein the conductor is adjacent to the liner and can bear against the liner;
- coupling the distal end of the conductor with the electrode; and
- coupling a terminal connector to the proximal end portion of the lead body and to the proximal end of the conductor.

17. The method of claim 16, wherein forming the insulative lead body includes:
- helically winding a ribbon of a first material around a mandrel to form the helical liner; and
- forming the insulative member by disposing a second material over the first material, the second material being different than the first material.

18. The method of claim 16, wherein forming the insulative lead body includes:
- forming the insulative member;
- helically winding a ribbon of a first material to form the helical liner; and
- disposing the helical liner within the lumen.

19. The method of claim 17, wherein the first material is a flexible, electrically insulating polymer.

* * * * *